(12) United States Patent
Kopsala

(10) Patent No.: US 6,731,717 B2
(45) Date of Patent: May 4, 2004

(54) METHOD FOR CEPHALOMETRIC IMAGING

(75) Inventor: Panu Kopsala, Tuusula (FI)

(73) Assignee: Instrumentarium Corp., Tuusula (FI)

( * ) Notice: Subject to any disclaimer, the term of this patent is extended or adjusted under 35 U.S.C. 154(b) by 0 days.

(21) Appl. No.: 10/204,104

(22) PCT Filed: Feb. 14, 2001

(86) PCT No.: PCT/FI01/00137

§ 371 (c)(1), (2), (4) Date: Oct. 10, 2002

(87) PCT Pub. No.: WO01/60257

PCT Pub. Date: Aug. 23, 2001

(65) Prior Publication Data

US 2003/0118147 A1 Jun. 26, 2003

(30) Foreign Application Priority Data

Feb. 18, 2000 (FI) .............................................. 20000369

(51) Int. Cl.⁷ ................................................ A61B 6/14
(52) U.S. Cl. .......................................... 378/38; 378/196
(58) Field of Search ....................... 378/38–40, 195–197

(56) References Cited

U.S. PATENT DOCUMENTS

| | | | |
|---|---|---|---|
| 4,661,967 A | 4/1987 | Nishikawa | 378/39 |
| 5,058,147 A | 10/1991 | Nishikawa et al. | 378/38 |
| 5,436,950 A | 7/1995 | Pauli et al. | 378/4 |
| 5,511,106 A | 4/1996 | Doebert et al. | 378/146 |
| 5,708,503 A | 1/1998 | Carrieri | 356/453 |

*Primary Examiner*—Craig E Church
(74) *Attorney, Agent, or Firm*—Andrus, Sceales, Starke & Sawall, LLP

(57) ABSTRACT

The invention relates to a method for cephalometric imaging using an apparatus (1) which comprises an X-ray source (5), a line detector camera (8) equipped with a digital detector, which line detector camera is located to a position far away from the X-ray source (5) for carrying out cephalometric imaging while the slot of the line detector camera is substantially vertical. In cephalometric imaging, an X-ray beam (11) located substantially on the vertical plane is directed from the X-ray source (5) through the object being imaged, and the X-ray source (5) is at the same time turned about the rotation center (13) located between the X-ray source and the line detector camera (8) in order to scan the object being imaged in the horizontal direction, whereby the line detector camera (8) is moved during the scanning movement in such a way that the ray beam (11) meets the slot (14) of the line detector camera. In the method, the effective focal spot is transferred from the rotation center (13) to the focal spot of the X-ray source (5) by transferring the rotation center by means of a transverse linear movement (A) with respect to the ray beam (11).

1 Claim, 3 Drawing Sheets

METHOD FOR CEPHALOMETRIC IMAGING

CROSS REFERENCE TO RELATED APPLICATION

The present application is the U.S. national stage application of International Application PCT/FI01/00 137, filed Feb. 14, 2001, which international application was published on Aug. 23, 2001 as International Publication WO 01/60257. The International Application claims priority of Finnish Patent Application 20000369, filed Feb. 18, 2000.

SUMMARY OF THE INVENTION

The present invention relates to a method for cephalometric imaging using an apparatus which comprises an X-ray source, a line detector camera equipped with a digital detector, which line detector camera is located to a position far away from the X-ray source for carrying out cephalometric imaging while the slot of the line detector camera is substantially vertical, whereby in cephalometric imaging, an X-ray beam located substantially on the vertical plane is directed from the X-ray source through the object being imaged, and the X-ray source is at the same time turned about the rotation centre located between the X-ray source and the line detector camera in order to scan the object being imaged in the horizontal direction, whereby the line detector camera is moved during the scanning movement in such a way that the ray beam meets the slot of the line detector camera. The publication U.S. Pat. No. 5,511,106 discloses this type of scanning method for cephalometric imaging.

BRIEF DESCRIPTION OF THE INVENTION

When cephalometric imaging is carried out in the manner described in the preamble, the vertical ratio of enlargement remains the same as without the scanning movement, but the horizontal ratio of enlargement, on the other hand, changes because the rotation centre changes into the effective focal spot instead of the focal spot of the X-ray source. Accordingly, the object of the present invention is to provide a method by means of which the ratios of enlargement in cephalometric imaging can be maintained the same in the vertical and horizontal directions in cephalometric imaging, which is carried out by means of the turning movement taking place about the rotation centre of the X-ray source. A further object is to provide a method which can be implemented by using existing panoramic X-ray imaging apparatuses, which already comprise the means needed to perform the required movements. To achieve this object, the method relating to the invention is characterised in that in the method, the effective focal spot is transferred from the rotation centre to the focal spot of the X-ray source by transferring the rotation centre by means of a transverse linear movement with respect to the ray beam

BRIEF DESCRIPTION OF THE DRAWING

The invention is described in greater detail in the following, with reference to the accompanying drawings, in which.

DETAILED DESCRIPTION OF THE INVENTION

Figure 1:
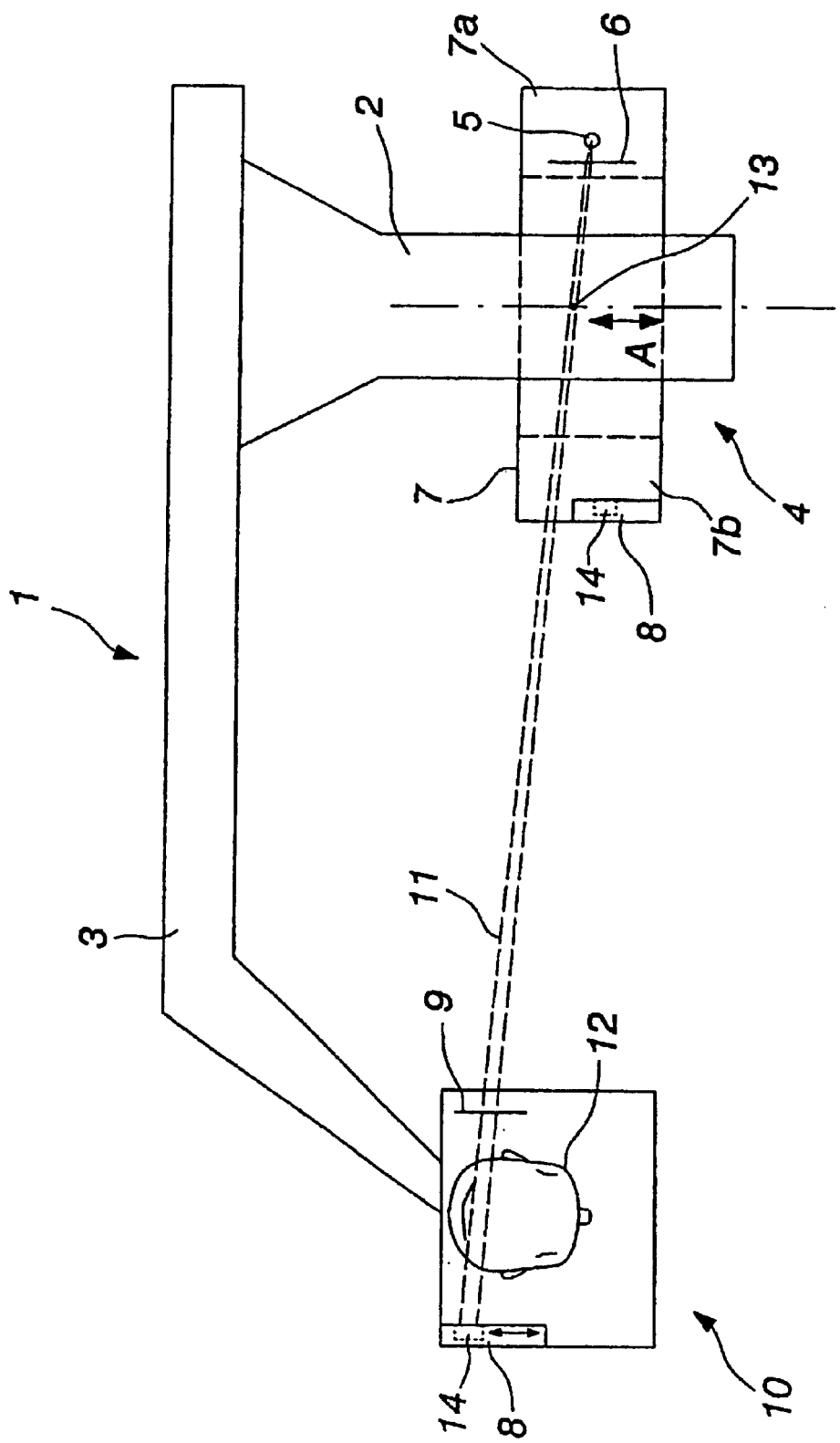
FIG. 1 shows a diagrammatic top view of an apparatus applicable for the method according to the invention.

The apparatus 1 according to FIG. 1 comprises a support part 2, beneath which is connected a panoramic imaging apparatus 4 which turns in a pivoting manner around the rotation centre 13, the imaging apparatus comprising a C arm 7, on one vertical branch 7a of which is arranged an X-ray source 5 and the primary collimator 6 in its vicinity, and on the other branch 7b a line detector camera 8.

Figure 2:
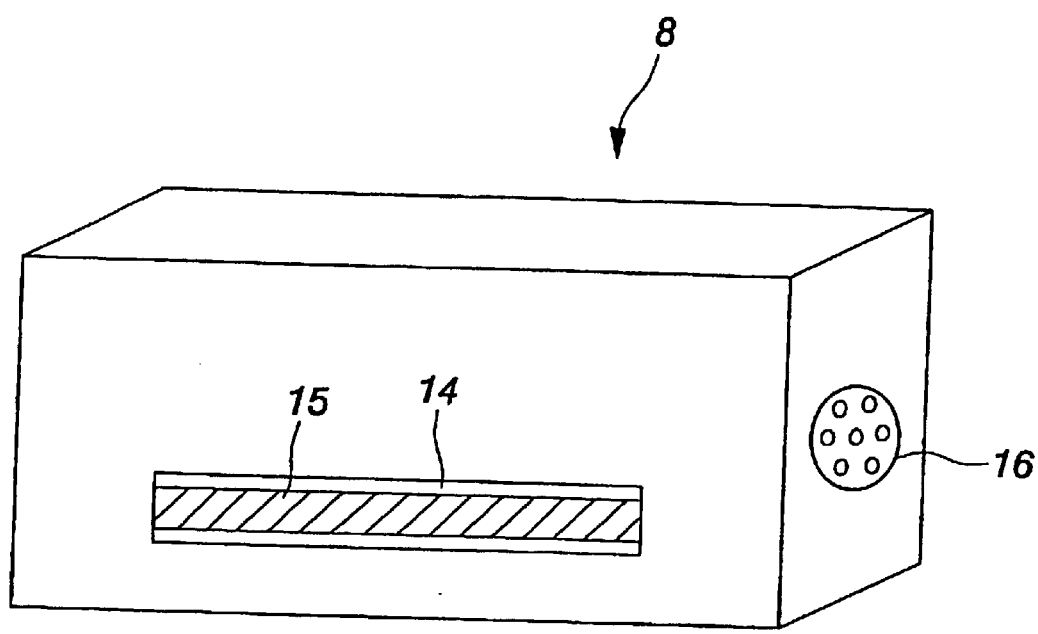
FIG. 2 shows diagrammatically a view in principle of a camera used in the apparatus according to FIG. 1.

FIG. 2 shows diagrammatically one implementation of a line detector camera 8, wherein on one side of the camera is formed a slot 14, behind which, inside the camera 8, is a digital detector 15, for example, a CCD sensor. The panoramic imaging apparatus 4 and its operation are, as such, known to a person skilled in the art. In panoramic imaging, the object to be imaged is placed between the branch parts 7a, 7b of the C arm by means of appropriate guides and supports, after which the X-ray source 5 is switched on and the C arm is rotated about the rotation centre 13, whereby the aperture of the primary collimator 6 is selected in such a way that the ray beam 11, which is substantially on the vertical plane, is directed at the detector 15 behind the substantially vertical slot 14 of the line detector camera 8 on the branch part 7b of the C arm 7, from which detector the image data is transmitted further, for example, to a microprocessor. This process of panoramic imaging will not be described in greater detail in this connection.

To the support part 2 is connected a supporting arm 3, at the other end of which is the cephalometric imaging apparatus 10, which comprises a line detector camera 8 to be placed behind the object being imaged, and a secondary collimator 9 to be placed in front of the object being imaged. In cephalometric imaging, the patient's head is scanned by means of the ray beam 11 from right to left or vice versa.

Figure 3:
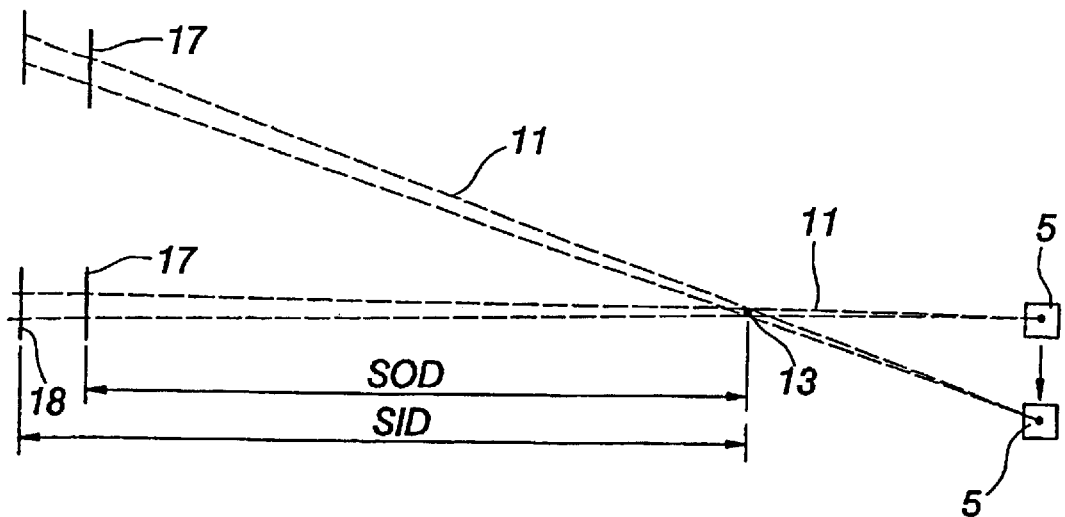
FIG. 3 shows diagrammatically the effect of the rotary movement of the X-ray source on the effective focus.

In the method according to the invention, cephalometric imaging is carried out by turning the X-ray source 5 about a rotation centre 13 to image the patient's head 12 by means of a vertically positioned ray beam 11. FIG. 3 shows a situation where the rotation centre 13 remains in place, in which case, when the X-ray source 5 turns about the rotation centre, the X-ray beams 11 travel in each angular position via the rotation centre 13, whereby the rotation centre 13 becomes the effective focal spot for the radiation coming through the object in the layer 17 being imaged on the image plane (detector) 18. In this case, the ratio of enlargement, which is determined by the ratio of the distance (SID) between the focus and the image plane to the distance (SOD) between the focus and the object, is the ratio of the distance between the rotation centre 13 and the image layer 17 to the distance between the rotation centre 13 and the image plane 18.

Figure 4:
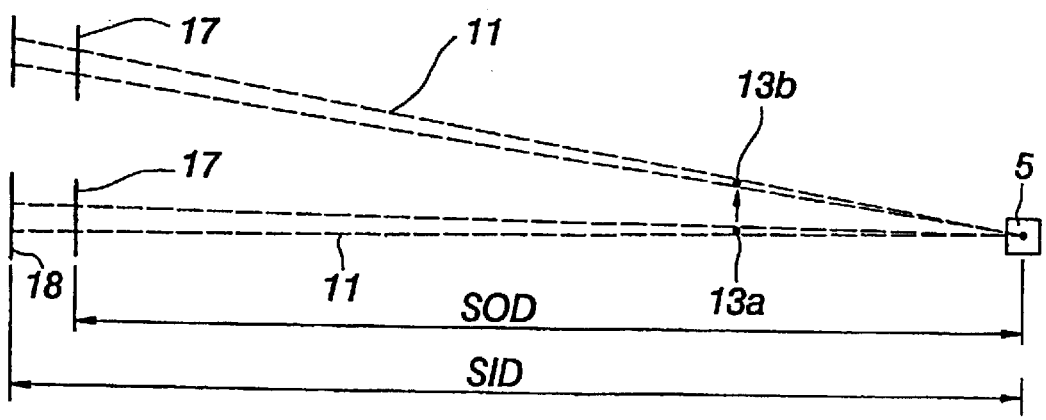
FIG. 4 shows diagrammatically the effect of the transfer of the rotation centre of the rotary movement of the X-ray source on the effective focus.

It is for this reason that, according to the invention, in cephalometric imaging the rotation centre 13 is arranged to be transferred by linear movement transversely with respect to the ray beam 11, as shown by reference marking A in FIG. 1. FIG. 4 shows a situation where the rotation centre has been transferred by linear movement from position 13a to position 13b, whereby the focal spot is transferred to the X-ray source 5, in which case also the horizontal ratio of enlargement remains the same.

What is claimed is:

1. A method for cephalometric imaging using an apparatus (1) which comprises an X-ray source (5), a line detector camera (8) equipped with a digital detector, which camera is located to a position far away from the X-ray source (5) for carrying out cephalometric imaging while the slot of the line detector camera is substantially vertical, whereby in cephalometric imaging, an X-ray beam (11) located substantially on the vertical plane is directed from the X-ray source (5) through the object being imaged, and the X-ray source is at the same time turned about the rotation centre (13) located between the X-ray source and the line detector camera (8) in order to scan the object being imaged in the horizontal direction, whereby the line detector camera (8) is moved during the scanning movement in such a way that the ray beam (11) meets the slot (14) of the line detector camera, characterised in that in the method, the effective focal spot is transferred from the rotation centre (13) to the focal spot of the X-ray source (5) by transferring the rotation centre by means of a transverse linear movement (A) with respect to the ray beam (11).

* * * * *